United States Patent
Soykan et al.

(10) Patent No.: US 6,824,561 B2
(45) Date of Patent: *Nov. 30, 2004

(54) IMPLANTABLE SYSTEM WITH DRUG-ELUTING CELLS FOR ON-DEMAND LOCAL DRUG DELIVERY

(75) Inventors: Orhan Soykan, New Brighton, MN (US); Maura G. Donovan, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/745,144

(22) Filed: Dec. 20, 2000

(65) Prior Publication Data

US 2001/0000802 A1 May 3, 2001

Related U.S. Application Data

(60) Division of application No. 09/144,420, filed on Aug. 31, 1998, now Pat. No. 6,206,914, which is a continuation-in-part of application No. 09/070,480, filed on Apr. 30, 1998, now abandoned.

(51) Int. Cl.⁷ ............................. A61F 2/06; A61B 19/00
(52) U.S. Cl. .................................. 623/1.42; 604/891.1
(58) Field of Search ........................ 623/1.42, 11.11, 623/66, 23.64; 604/891.1, 890.1, 65, 66, 67; 128/898

(56) References Cited

U.S. PATENT DOCUMENTS

| | | | |
|---|---|---|---|
| 3,523,807 A | 8/1970 | Gerendas | 106/124 |
| 4,146,029 A | 3/1979 | Ellinwood, Jr. | 128/260 |
| 4,476,868 A | 10/1984 | Thompson | 128/419 PG |
| 4,540,573 A | 9/1985 | Neurath et al. | 424/85 |
| 4,548,736 A | 10/1985 | Muller et al. | 252/315.1 |
| 4,556,063 A | 12/1985 | Thompson et al. | 128/419 PT |
| 4,733,665 A | 3/1988 | Palmaz | 128/343 |
| 4,753,635 A | 6/1988 | Sagen et al. | 604/49 |
| 4,800,882 A | 1/1989 | Gianturco | 128/343 |
| 4,821,723 A | 4/1989 | Baker, Jr. et al. | 128/419 |
| 4,886,062 A | 12/1989 | Wiktor | 128/343 |
| 4,911,717 A | 3/1990 | Gaskill, III | 623/11 |
| 4,944,659 A | 7/1990 | Labbe et al. | 418/322 |
| 5,102,417 A | 4/1992 | Palmaz | 606/195 |
| 5,144,949 A | 9/1992 | Olson | |
| 5,158,078 A | 10/1992 | Bennett et al. | 128/419 |
| 5,192,297 A | 3/1993 | Hull | 606/195 |
| 5,199,428 A | 4/1993 | Obel et al. | 128/419 |
| 5,207,218 A | 5/1993 | Carpentier et al. | 128/419 PG |
| 5,312,453 A | 5/1994 | Shelton et al. | 607/19 |
| 5,314,430 A | 5/1994 | Bardy | 607/5 |
| 5,330,507 A | 7/1994 | Schwartz | 607/14 |
| 5,342,348 A | 8/1994 | Kaplan | 604/891.1 |
| 5,354,316 A | 10/1994 | Keimel | 607/15 |
| 5,372,600 A | 12/1994 | Beyer et al. | 606/108 |
| 5,409,009 A | 4/1995 | Olson | 128/661.08 |
| 5,411,551 A | 5/1995 | Winston et al. | 623/1 |
| 5,419,760 A | 5/1995 | Narciso, Jr. | 604/8 |
| 5,429,634 A | 7/1995 | Narciso, Jr. | 604/890.1 |
| 5,510,077 A | 4/1996 | Dinh et al. | 264/485 |
| 6,206,914 B1 * | 3/2001 | Soykan et al. | 623/1.42 |

* cited by examiner

Primary Examiner—David J. Isabella
(74) Attorney, Agent, or Firm—Kenneth J. Collier (57) ABSTRACT

An implantable system that includes a carrier and eukaryotic cells, which produce and release a therapeutic agent, and a stimulating element for stimulating the release of the therapeutic agent. The system can also include a sensing element for monitoring a physiological condition and triggering the stimulating element to stimulate the delivery device to release the therapeutic agent. Alternatively, the patient in which the system is implanted can activate the stimulating element to release the therapeutic agent.

12 Claims, 4 Drawing Sheets

IMPLANTABLE SYSTEM WITH DRUG-ELUTING CELLS FOR ON-DEMAND LOCAL DRUG DELIVERY

This application is a divisional of application Ser. No. 09/144,420, filed Aug. 31, 1998, now U.S. Pat. No. 6,206,914, which is incorporated by reference.

FIELD OF THE INVENTION

The present invention relates to implantable systems that include medical devices (e.g., stents, vascular grafts, stent grafts) that function as a carrier for eukaryotic cells (e.g., genetically engineered endothelial cells). Such cells are capable of producing and releasing a therapeutic agent (e.g., tissue-type Plasminogen Activator) for on-demand localized treatment of conditions such as coronary artery disease. The cells or the device carrying them release the therapeutic agent upon the application of a stimulus (e.g., electrical stimulus).

BACKGROUND OF THE INVENTION

Coronary Artery Disease (CAD) affects 1.5 million people in the USA annually. About 10% of these patients die within the first year and the rest suffer from myocardial infarction and develop related symptoms, such as arrhythmias, CHF, and mechanical complications (e.g., aneursym, thrombus formation, pericarditis). During CAD, formation of plaques under the endothelial tissue narrows the lumen of the coronary artery and increases its resistance to blood flow, thereby reducing the $O_2$ supply. Injury to the myocardium (i.e., the middle and thickest layer of the heart wall, composed of cardiac muscle) fed by the coronary artery begins to become irreversible within 0.5–1.5 hours and is complete after 6–12 hours, resulting in a condition called myocardial infarction. If the ischemia due to stenosis of the coronary artery lumen could be reduced by increasing the blood circulation to the myocardium, the major cause of most of the heart disease would be eliminated.

Current and proposed treatments for coronary artery disease typically focus on pharmacological approaches and surgical intervention. For example, angioplasty, with and without stents, is a well known technique for reducing stenosis. Systemically administered drugs (e.g., anticoagulants) are also commonly used, however, such drugs become diluted, which can reduce their potency by the time they reach the remote site. Furthermore, systemic administration can be deleterious because it can lead to complications as a result of the high dosages required upon administration to allow for dilution that occurs during transport to the remote site. Therefore, localized delivery of therapeutic agents is preferred. Local delivery is advantageous in that the effective local concentration of delivered drug is much higher than can normally be achieved by systemic administration.

Stents have been used as delivery vehicles for therapeutic agents (i.e., drugs). Intravascular stents are generally permanently implanted in coronary or peripheral vessels. Stent designs include those of U.S. Pat. Nos. 4,733,655 (Palmaz), 4,800,882 (Gianturco), or 4,886,062 (Wiktor). Such designs include both metal and polymeric stents, as well as self-expanding and balloon-expandable stents. Stents are also used to deliver a drug (e.g., antiplatelet agents, anticoagulant agents, antimicrobial agents, antimetabolic agents) at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), for example. Anticoagulant substances such as heparin and thrombolytic agents have also been incorporated into a stent, as disclosed, for example, in U.S. Pat. Nos. 5,419,760 (Narciso, Jr.) and U.S. Pat. No. 5,429,634 (Narciso, Jr.). Stents have also been used to deliver viruses to the wall of a lumen for gene delivery, as disclosed in U.S. patent application Ser. No. 08/746,404, filed Nov. 8, 1996 (Donovan et al.).

Stents seeded with autologous endothelial cells (Dichek, et al., *Circulation*, 80, 1347–1353 (1989)) are disclosed as a method for delivering recombinant protein over time to the vascular wall. The concentration of secreted protein produced by the endothelial cells that is required to treat the surrounding vascular tissue can be significantly higher than could be tolerated if delivered systemically. However, in order to be effective, it is not only necessary to release a high dose of the drug, but it is also necessary to achieve controlled release, e.g., immediately after an occlusion. Thus, it would be desirable to control the release of such cellular components into the surrounding tissue when needed (i.e., on demand). The present invention provides such a system.

Many of the following lists of patents and nonpatent documents disclose information related to the local delivery of therapeutic agents using medical devices, such as stents. Others are directed toward stent designs and other medical devices as well as genetically engineered cells, for example.

TABLE 1a

Patents

| Patent No. | Inventor(s) |
| --- | --- |
| 3,523,807 | Gerendas |
| 4,476,868 | Thompson |
| 4,540,573 | Neurath et al. |
| 4,548,736 | Muller et al. |
| 4,556,063 | Thompson et al. |
| 4,733,655 | Palmaz |
| 4,800,882 | Gianturco |
| 4,821,723 | Baker et al. |
| 4,886,062 | Wiktor |
| 4,944,659 | Labbe et al. |
| 5,102,417 | Palmaz |
| 5,131,388 | Pless |
| 5,144,949 | Olson |
| 5,158,078 | Bennett et al. |
| 5,192,297 | Hull |
| 5,199,428 | Obel et al. |
| 5,207,218 | Carpentier et al. |
| 5,312,453 | Shelton et al. |
| 5,314,430 | Bardy |
| 5,330,507 | Schwartz |
| 5,354,316 | Keimel |
| 5,372,600 | Beyer et al. |
| 5,409,009 | Olson |
| 5,419,760 | Narciso, Jr. |
| 5,429,634 | Narciso, Jr. |
| 5,510,077 | Dinh et al. |
| 5,545,186 | Olson et al. |
| 5,674,722 | Mulligan et al. |
| 5,702,427 | Ecker et al. |
| U.S. Pat. Appl. 08/746,404, filed Nov. 8, 1996 | Donovan et al. |

TABLE 1b

Foreign Patent Documents

| Document No. | Applicant | Publication Date |
|---|---|---|
| WO 90/13332 | Cedars-Sanai Medical Ctr. | Nov. 15, 1990 |
| WO 91/12779 | Medtronic, Inc. | Sep. 5, 1991 |
| WO 96/28841 | Smela et al. | Sep. 19, 1996 |
| WO 96/34417 | Smela et al. | Oct. 31, 1996 |

TABLE 1c

Nonpatent Documents

Bansal et al., "Calcium-Regulated Secretion of Tissue Plasminogen Activator and Parathyroid Hormone from Human Parathyroid Cells," J. Clin. Endocrin. Metab., 74, 266–271 (1992).
"Bioartificial Polymeric Materials Obtained from Blends of Synthetic Polymers with Fibrin and Collagen", International Journal of Artificial Organs, 14(5) (1991).
Blaese et al., "T Lymphocyte-Directed Gene Therapy for ADA SCID: Initial Trial Results After 4 Years," Science 270, 475–480 (1995).
Bordignon et al., "Gene Therapy in Peripheral Blood Lymphocytes and Bone Marrow for ADD Immunodeficient Patients," Science, 270, 470–475 (1995).
Bouaziz et al., "Effect of constant and modulated electrical charges applied to the culture material on PGI2 and TXA2 secretion by endothelial cells," Biomaterials, 16, 727–734 (1995).
Bouaziz et al., "Vascular endothelial cell responses to different electrically charged poly(vinylidene fluoride) supports under static and oscillating flow conditions," Biomaterials, 18, 107–112 (1997).
Braunwald et al., "Unstable Angina: Diagnosis and Management," Clinical Practical Guidelines, No. 10, U.S. Department of Health and Human Services, Public Health Services, Agency for Health Care Policy and Research, AHCPR Publication No. 94-0602, 27–92 (1994).
Bugiardini et al., "Relation of Severity of Symptoms to Transient Myocardial Ischemia and Prognosis in Unstable Angina," J. Am. Coll. Cardiol., 25, 597–604 (1995).
Chowdhury et al., "Long-Term Improvement of Hypercholesterolemia After ex Vivo Gene Therapy in LDLR-Deficient Rabbits," Science, 254, 1802–1804 (1991).
Dicheck et al., "Enhanced In Vivo Antithrombotic Effects of Endothelial Cells Expressing Recombinant Plasminogen Activators Transduced With Retroviral Vectors," Circulation, 93, 301–309 (1996).
Dicheck et al., "Seeding of Intravascular Stents With Genetically Engineered Endothelial Cells," Circulation, 80, 1347–1353 (1989).
Dicheck et al., "Retroviral Vector-mediated Gene Transfer into Endothelial Cells," Mol. Biol. Med., 8, 257–266 (1991).
Dunn et al., "Seeding of Vascular Grafts With Genetically Modified Endothelial Cells," Circulation, 93, 1439–1446 (1996).
Ekterae et al., "Retroviral vector-mediated transfer and expression of human tissue plasminogen activator gene in human endothelial and vascular smooth muscle cells," J. Vascular Surgery, 21, 953–962 (June 1995).
Fisher et al., "Isolation and Characterization of the Human Tissue-type Plasminogen Activator Structural Gene Including Its 5' Flanking Region," J. Biol. Chem., 260, 11223–11230 (1985).
Gillis et al., "Secretion of Prostacyclin, Tissue Plasminogen Activator and its Inhibitor by Cultured Adult Human Endothelial Cells Grown on Different Matrices," Eur. J. Vasc. Endovasc. Surg., 11, 127–133 (1996).
Grossman et al., "Successful ex vivo gene therapy directed to liver in a patient with familial hypercholesterolaemia," Nature Genetics, 6, 335–341 (1994).
Innis et al. eds., "PCR Strategies", Academic Press, New York, New York (1995).
Kohn et al., "Engraftment of gene-modified umbilical cord blood cells in neonates with adenosine deaminase deficiency," Nature Medicine, 1, 1017–1023 (1995).
Levin et al., "Protein Kinase C and the Stimulation of Tissue Plasminogen Activator Release from Human Endothelial Cells," J. Biol. Chem., 264, 16030–16036 (1989).
Lilly, "Acute Myocardial Infarction", Pathophysiology of Heart Disease, Lea & Febiger, Philadelphia, PA, Ch. 7, 113–129 (1993).
Nabel et al., "Recombinant Gene Expression in Vivo Within Endothelial Cells of the Arterial Wall," Science, 244, 1342–1344 (1989).
Nilius et al., "Activation of a Cl⁻ Current by Hypotonic Volume Increase in Human Endothelial Cells," J. Gen. Phys., 103 787–805 (1994).

TABLE 1c-continued

Nonpatent Documents

Ryan et al., "ACC/AHA Guidelines for the Management of Patients With Acute Myocardial Infarction: A Report of the American College of Cardiology/American Heart Association Task Force on Practice Guidelines (Committee on Management of Acute Myocardial Infarction)," J. Am. Coll. Cardiol., 28, 1328–1428 (1996).
Sambrook et al, "Molecular Cloning: A Laboratory Manual", Cold Spring Harbor Laboratory Press, Cold Spring Harbor, New York, New York (1989).
Santell et al., "Cyclic AMP Potentiates Phorbol Ester Stimulation of Tissue Plasminogen Activator Release and Inhibits Secretion of Plasminogen Activator Inhibitor-1 from Human Endothelial Cells," J. Biol. Chem., 263, 16802–16808 (1988).
Smela et al., "Controlled Folding of Micrometer-Size Structures," Science, 268, 1735–1738 (1995).
Van den Eijnden-Schrauwen et al., "Studies on the Acute Release of Tissue-Type Plasminogen Activator from Human Endothelial Cells In Vitro and in Rats In Vivo: Evidence for a Dynamic Storage Pool," Blood, 85, 3510–3517 (1995).
Williams et al., "Introduction of new genetic material into pluripotent haematopoietic stem cells of the mouse," Nature, 310, 476–480 (1984).
Yanagisawa et al., "The Human Preproendothelin-1 Gene: Possible Regulation by Endothelial Phosphoinositide Turnover Signaling," J. Cardiovasc. Pharmacol., 13, S13–S17 (1989).

All patent and nonpatent documents listed in Table 1 are hereby incorporated by reference herein in their respective entireties. As those of ordinary skill in the art will appreciate upon reading the Summary of the Invention, Detailed Description of Preferred Embodiments, and Claims set forth below, many of the systems, devices, and methods disclosed in these documents may be modified advantageously by using the teachings of the present invention.

SUMMARY OF THE INVENTION

The present invention provides implantable systems that include delivery devices having a carrier and eukaryotic cells associated therewith, optionally within a containment vehicle. Such cells are capable of producing at least one therapeutic agent (i.e., drug), which is released from the delivery device upon the application of a stimulus (e.g., electrical stimulus) for on-demand (i.e., when needed) localized treatment of conditions such as coronary artery disease or cerebral vascular occlusion, for example. The cells are referred to herein as "drug-eluting" cells.

Release of the therapeutic agent from the delivery device is stimulated by a variety of methods, including electrical stimulation, which can be used to create an electrical field or mechanical stimulus, for example. This can be accomplished by direct action on the cells, such as by stimulating the cellular membrane to release the cellular products contained therein. Alternatively, this can be accomplished by activating the cellular products such that upon release they will function as therapeutic agents. This can also be accomplished by stimulating a microscopic containment vehicle that contains the cells, such as by stimulating a synthetic membrane of the containment vehicle, to release the cells and/or their cellular products.

Thus, an object of the present invention is to provide a system and method for the treatment (including prevention) of coronary artery disease, for example, by producing and delivering locally a therapeutic agent, such as an anticoagulant. Significantly, the local dosage can be controlled and provided on demand without worrying about the systemic effects. Furthermore, the local dosage can be administered prior to significant physiological damage occurs to the patient.

In a preferred embodiment, the present invention provides an implantable system that includes: a delivery device comprising a carrier for carrying eukaryotic cells that produce at least one therapeutic agent; a stimulating element for stimulating the release of the therapeutic agent from the delivery device; and a sensing element for monitoring at least one physiological property of a patient in which the system is implanted and communicating with the stimulating element to stimulate the release of the therapeutic agent from the delivery device.

In another embodiment, an implantable system includes a delivery device comprising an intraluminal stent, which includes a lumen-wall contacting surface, a lumen-exposed surface, a first polymer composition covering at least a portion of the stent (preferably, at least a portion of the lumen-exposed and the lumen-wall contacting surfaces), and endothelial cells associated with the first polymer composition covering, wherein the endothelial cells produce at least one therapeutic agent. The implantable system further includes an electrical stimulating element for stimulating the release of the therapeutic agent from the delivery device, and a sensing element for monitoring at least one physiological property of a patient in which the system is implanted and communicating with the electrical stimulating element to stimulate the release of the therapeutic agent from the delivery device.

The present invention also provides a method of local delivery (as opposed to systemic delivery) of a therapeutic agent. The method involves simply implanting an implantable system described above. Once implanted into a patient, the therapeutic agent is released from the delivery device when the sensing element detects a predetermined level of a physiological property (e.g., a certain pH or level of blood flow or blood gases) and communicating with the stimulating element to trigger the release.

A method of making an implantable system for local delivery of a therapeutic agent is also included within the scope of the present invention. The method includes: providing a delivery device comprising a carrier and eukaryotic cells associated therewith that produce at least one therapeutic agent; providing a stimulating element for stimulating the release of the therapeutic agent from the delivery device; providing a sensing element for monitoring at least one physiological property of a patient in which the system is implanted; and connecting the stimulating element and sensing element such that they communicate with each other to stimulate the release of the therapeutic agent from the delivery device when implanted in the body of a patient and the sensing element detects a predetermined level of a physiological property. Preferably, the step of providing a delivery device includes: providing a carrier; isolating eukaryotic cells from a patient; culturing the eukaryotic cells; delivering nucleic acid of a desired therapeutic agent to the eukaryotic cells to form genetically engineered eukaryotic cells; and contacting the carrier with the genetically engineered eukaryotic cells.

In an alternative embodiment, the present invention provides implantable systems as described above without the sensing element. In such systems, the patient in which the system is implanted activates the stimulating element when desired (i.e., on demand). Typically, this occurs when the patient detects a change in a physiological condition (e.g., angina) and communicates with the electrical stimulating element to trigger release of the therapeutic agent. The patient can communicate with the electrical stimulating element to activate it using radio frequency, infrared, or acoustic pulses.

BRIEF DESCRIPTION OF THE DRAWINGS

FIG. 2 is an illustration of an implantable system according to the present invention that includes the use of an RF signal to communicate and generate an electrical current in a coiled stent. Inset

DETAILED DESCRIPTION OF THE PREFERRED EMBODIMENTS

The present invention provides implantable systems for the treatment (including prevention) of a variety of disorders, such as, coronary artery disease, which can be manifested by stenosis, myocardial infarction, aneurysm, angina, and/or atherosclerosis, or cerebro-vascular occlusion, which can result in a stroke, for example. The implantable systems of the present invention include a delivery device comprising a carrier (e.g., stents, vascular grafts, stent grafts) and eukaryotic cells (e.g., genetically engineered endothelial cells), which can optionally be enclosed within containment vehicles. Such cells are capable of producing one or more therapeutic agents (e.g., proteins and other cellular products) that have a preventative, therapeutic, or disease-treating effect on surrounding tissue.

The therapeutic agents are released from the delivery device upon the application of a stimulus (e.g., electrical stimulus). This can occur as a result of the stimulus acting directly on the cells to cause them to produce, activate, and/or release the therapeutic agents. Alternatively, this can occur as a result of the stimulus acting on the optional containment vehicles within the delivery device, for example. Significantly, the local dosage can be controlled and provided on demand without worrying about the systemic effects, and before significant damage occurs to the heart muscle, for example.

Figure 1:
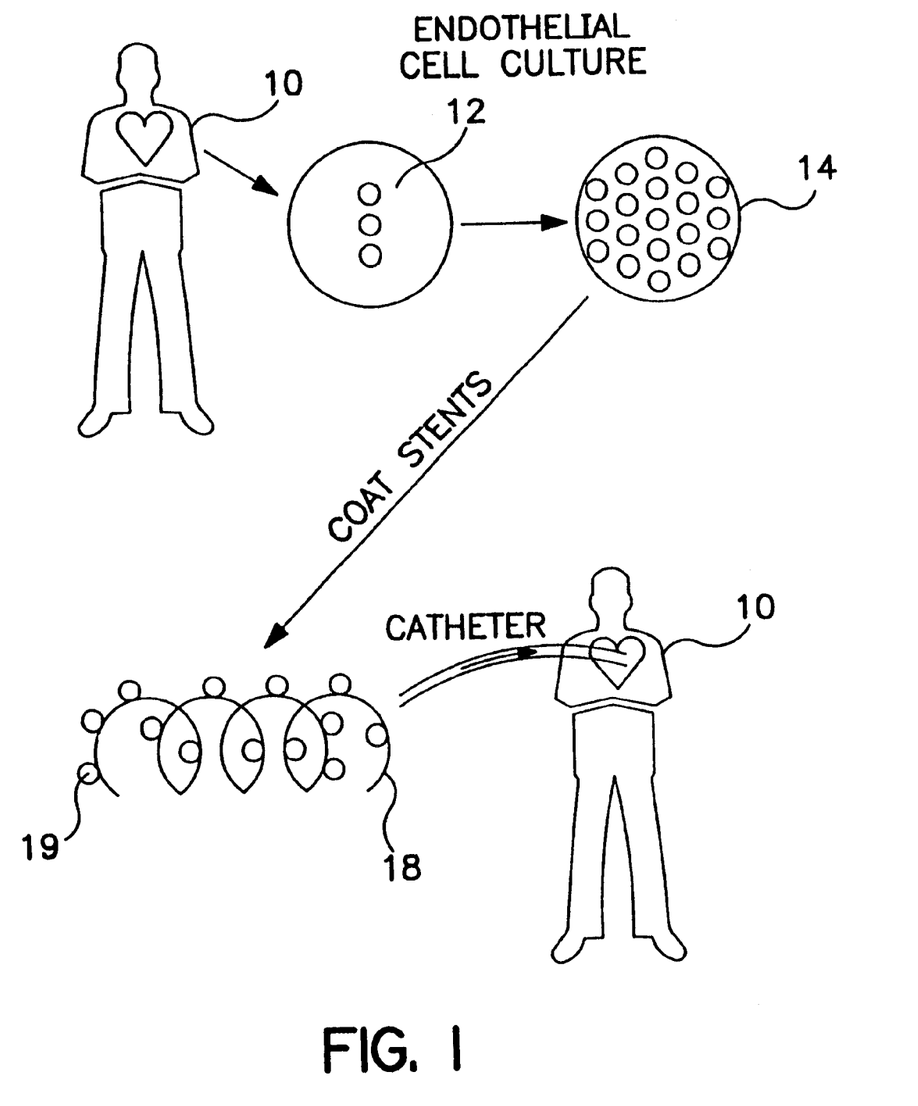
FIG. 1 is an illustration of a method of making and implanting a drug-loaded stent of the present invention.

Referring to FIG. 1, in one preferred embodiment, endothelial cells 12 are obtained from a patient 10 and grown in cell culture 14. During proliferation in cell culture 14, cells are infected with a genetically engineered retrovirus which integrates the gene for the drug to be locally delivered into the chromosomes of the endothelial cells. A cylindrical coil shaped stent 18 is produced out of a conductive metal and coated with an insulative material, such as an organic polymer, except at its ends, and with genetically engineered endothelial cells 19. The stent 18 coated with endothelial cells is introduced into the patient 10. Typically, the coated stent is implanted into the appropriate coronary artery during a catheterization procedure, into the right or left coronary artery depending on the pathophysiology.

Referring to FIG. 2, a preferred embodiment of the implantable system 20 of the present invention includes, in addition to the coated stent 18, a stimulation device 22 that includes, for example, an implantable generator, which can be implanted in the left pectoralis major area, a traditional pacemaker implant site, along with an isolated lead or antenna 24 traveling to the right ventricle via the subclavian vein, superior vena cava, and tricuspid valve, a traditional pacemaker lead placement technique. The stimulation device 22 can monitor the patient (using a sensing element incorporated within the device 22), if desired, and trigger the stent (using a stimulating element incorporated within device 22) with engineered endothelial cells to release the cellular product(s). Typically, as is shown in this embodiment, the stimulation device is remote from the delivery device.

Alternatively, the patient can control the stimulation device and cause the stent to release the therapeutic agent(s) upon sensing a physiological change (e.g., angina) using a patient activator to communicate with the stimulating element. In this embodiment, the stimulation device does not need a sensing element; rather, the patient acts as the sensor to detect an undesirable or a change in a physiological condition. Such patient activators can involve the use of radio frequency, infrared, acoustic pulsed, or magnetic means. For example, upon experiencing angina (i.e., chest pain), a patient can hold a hand-held device in place over the implant site of the stimulating element (e.g., an implantable pulse generator) to communicate with it and activate it to stimulate the remote endothelial cells.

The sensing element can be in the form of electrocardiogram (ECG) for monitoring changes in the circulatory system, such as a reduction of blood flow in the coronary sinus, for example. A sudden change in ECG morphology such as ST segment elevation is usually due to the onset of ischemia caused by a decrease in flow due to an occlusion resulting from the rupture of an unstable plaque (i.e., a blood clot). Other sensors, such as blood gas sensors, for example, can alternatively or additionally be used to detect changes in a patient's coronary circulatory system. Once the onset of ischemia is detected, an implantable pulse generator (IPG), for example, will trigger the delivery device (preferably, by stimulating the endothelial cells) to release one or more cellular products (e.g., tissue-type Plasminogen Activator or t-PA) to dissolve the clot and prevent the infarction from taking place.

In one preferred embodiment, as illustrated by FIG. 2, when it is time to reduce the coagulation in a coronary artery (as determined by a sensing element in an implantable stimulation device 22 or by a patient experiencing angina), a radio frequency signal 26 is sent to the coil formed by the stent 18. Because the ends of the stent 18 are not insulated, electromotive force (EMF) generated by the RF signal is delivered to the drug-eluting cells. Upon that event, the cells, e.g., genetically engineered endothelial cells, can be stimulated to release their stores of thrombolytic agents, such as tissue-type plasminogen activator, immediately.

Placement of genetically engineered endothelial cells, for example, upstream in the coronary artery will allow the secretion of various therapeutic agents (i.e., drugs) into the lumen, and the blood will carry them through the rest of the circulatory system. Although this eventually results in more of a systemic delivery, the administration of the therapeutic agent is initiated as local delivery at the site of the delivery device. Release of tissue-type plasminogen activator (t-PA) by engineered endothelial cells in a coronary artery would allow a potent dose of the drug to be delivered locally while avoiding dilution, and potential toxicity as in the case of systemic administration of the same drug. Ideally, this system will dissolve blood clots, for example, as soon as they form through the localized delivery of potent quantities of t-PA, for example, upstream from the site of thrombus formation.

Drug-Eluting Cells

Cells suitable for use in the present invention include a wide variety of eukaryotic cells that produce therapeutic agents, or can be genetically engineered to produce therapeutic agents. Ideally, such cells are also able to secrete these agents, particularly upon the application of a stimulus, such as an electrical stimulus. Suitable cells for use in the present invention typically include mesenchymal or mesodermal cells, including, but not limited to endothelial cells and fibroblasts, whether they are autologous or allogeneic, genetically engineered or nonengineered. Mixtures of such cells can also be used. Endothelial cells are particularly suitable for use in the present invention because they line the walls of the blood vessels. They are also particularly suitable for use in the present invention because they are capable of secreting vasodilatory, thrombolytic, or angiogenic factors, which can facilitate recovery of ischemic myocardium.

Endothelial cells and fibroblasts are preferred because they have been shown to be suitable for use in ex vivo gene transfer. Ex vivo gene transfer (also referred to herein as ex vivo gene therapy) is a process by which cells are removed from the body using well known techniques, genetically manipulated, usually through transduction or transfection of nucleic acid into the cells in vitro, and then returned to the body for therapeutic purposes. This contrasts with in vivo gene therapy, where a gene transfer vector is administered to the patient resulting in genetic transfer into cells and tissues in the intact patient. Ex vivo techniques are well known to one of skill in the art.

Ex vivo gene therapy is an effective approach because the target cells to be used in the procedure can be manipulated as needed to optimize gene transfer efficiency and thus the effectiveness of the overall procedure. However, the ex vivo approach can only be utilized for those cell types which can be readily retrieved from the body, cultured ex vivo, and then returned to the body. Such cells include blood and marrow cells, liver hepatocytes, skin fibroblasts, muscle myoblasts, and vascular endothelial cells. Thus, endothelial cells and fibroblasts, which can be efficiently infected by retroviral vectors in vitro, and then transplanted back into the host to achieve gene transfer in vivo, are particularly preferred for use in the present invention.

Autologous endothelial cells are particularly desirable. Vascular endothelial cells have been removed from a patient and transduced ex vivo with a retroviral vector designed for expression of β-galactosidase as a reporter gene, as disclosed in Nabel et al., *Science*, 244, 1342–1344 (1989). Such genetically engineered cells can be reintroduced into a patient. For example, Nabel et al. showed that endothelial cells engineered to express β-galactosidase could be introduced into an occluded vascular site using a balloon catheter, after which the presence of engrafted endothelial cells could be detected by staining for β-galactosidase activity.

In one embodiment of the present invention, endothelial cells are obtained from a patient and grown in cell culture. During proliferation in cell culture, they are infected with a genetically engineered retrovirus which integrates the gene for the drug to be locally delivered into the chromosomes of the endothelial cells. This can be accomplished, for example, according to the teachings of U.S. Pat. No. 5,674,722 (Mulligan et al.) and Dichek et al., *Mol. Biol. Med.*, 8, 257–266 (1991). For the treatment of coronary artery disease (CAD), candidate genes include the gene encoding wild-type tissue plasminogen activator and the gene encoding protein C, for example. The isolation and characterization of the human t-PA structural gene is disclosed in Fisher et al., *J. Biol. Chem.*, 260, 11223–11230 (1985).

Activated Protein C degrades the coagulation factors which are responsible for the formation of life threatening clots in the coronary arteries. However, protein C requires the presence of $Ca^{++}$ (calcium ion) for its own activation, which is controlled in the cells by ion gates which, in turn, are under the control of the voltages across the cell membrane. Thus, electrical stimulation of the cells can activate protein C. For example, endothelial cells may be depolarized, thereby altering the ion concentrations within the cells. Although the inventors do not wish to be bound by theory, it is believed that changing ion concentration, such as calcium ion concentration, may trigger secretion of certain cellular products, such as t-PA. Alternatively, calcium ions can activate protein C, which can start the cascade for the reduction of coagulation factors and prevent the formation of clots.

There are a wide variety of methods that can be used to deliver nucleic acid to the eukaryotic cells if they are to be modified to secrete a desired agent. These are well known to one of skill in the art. The desired nucleic acid can be inserted into an appropriate delivery vehicle, such as, for example, an expression plasmid, cosmid, YAC vector, and the like. There are a number of viruses, live or inactive, including recombinant viruses, that can also be used. A retrovirus can be genetically modified to deliver any of a variety of genes. Adenovirus has been used in a variety of experiments to deliver nucleic acid capable of directing and expressing protein in a cell. These include, but are not limited to, superoxide dismutase, tissue plasminogen activator, and interleukin-10.

Exemplary nucleic acid that would function as nucleic acid for incorporation into the cells include, but are not limited to, nucleic acid operably encoding a protein, polypeptide, or peptide to deliver a therapeutic effect to a cell. The nucleic acid can include an entire gene or a portion of a gene. Exemplary genes include, but are not limited to, the active form of the nitric oxide synthase (a protein that is known to relax blood vessels and prevent clot formation), and prostaglandin H synthase (to restore an endogenous inhibitor of platelet aggregation and vasoconstriction following injury to endothelium).

There are a variety of disorders that can be treated using the systems and devices of this invention. Examples of these disorders include, but are not limited to, damage associated with myocardial infarction or aneurysms (targeting fibroblast growth factor or transforming growth factor β and protease, respectively), atherosclerosis (targeting high density lipoprotein), and hypercoagulable states (targeting tissue-plasminogen activator).

The gene sequence of the nucleic acid delivered by the virus, including nucleic acid encoding proteins, polypeptide or peptide is available from a variety of sources including GenBank (Los Alamos National Laboratories, Los Alamos, N.Mex.), EMBL databases (Heidelberg, Germany), and the University of Wisconsin Biotechnology Center, (Madison, Wis.), published journals, patents and patent publications. All of these sources are resources readily accessible to those of ordinary skill in the art. The gene sequence can be obtained from cells containing the nucleic acid fragment (generally, DNA) when a gene sequence is known. The nucleic acid can be obtained either by restriction endonuclease digestion and isolation of a gene fragment, or by polymerase chain reaction (PCR) using oligonucleotides as primers either to amplify cDNA copies of mRNA from cells expressing the gene of interest or to amplify cDNA copies of a gene from gene expression libraries that are commerically available. Oligonucleotides or shorter DNA fragments can be prepared by known nucleic acid synthesis techniques and from commercial suppliers of custom oligonucleotides such as Amitof Biotech Inc. (Boston, Mass.), or the like. Those skilled in the art will recognize that there are a variety of commercial kits available to obtain cDNA from mRNA (including, but not limited to Stratagene, La Jolla, Calif. and Invitrogen, San Diego, Calif.). Similarly, there are a variety of commercial gene expression libraries available to those skilled in the art including libraries available form Stratagene, and the like. General methods for cloning, polymerase chain reaction and vector assembly are available from Sambrook et al. eds. (*Molecular Cloning: A Laboratory Manual*, 1989 Cold Spring Harbor Laboratory Press, Cold Spring Harbor, N.Y.) and Innis, et al. eds. (*PCR Strategies*, 1995, Academic Press, New York, N.Y.).

Depending on the maximum genome size that a particular viral genome can accommodate or that can be associated with a virus particle, the virus delivering nucleic acid to the cell can include nucleic acid encoding one or more proteins, polypeptides, or peptides. Oligonucleotides can be delivered by virus through the incorporation of oligonucleotides within the virus or associated with the outer surface of the virus using methods well known to one of skill in the art.

Therapeutic agents (i.e., drugs) that can be produced, stored, and secreted by eukaryotic cells, particularly genetically engineered endothelial cells, include, but are not limited to, anticoagulant agents, antiplatelet agents, antifibrinolytic agents, angiogenesis factors, etc. Specific examples include activated protein C, tissue plasminogen activator, prostacyclin, and vascular endothelial growth factor (VEGF). Such cells are referred to herein as "drug-eluting" cells.

The drug-eluting cells can be coated directly on the carrier of the delivery device or they can be incorporated into the carrier, as in a polymer film (i.e., sheeting) or coating on a stent. They can also be included within a microscopic containment vehicle that can be stimulated to release the cells and/or their cellular products. The microscopic containment vehicle can be coated on the carrier or incorporated into the carrier, as in a polymer film or coating on a stent. The cells can be induced to produce, activate, and/or release their cellular products (including one or more therapeutic agents) by an external stimulation device. This can occur as a result of destruction of the cellular membrane, for example. Alternatively, cells can constitutively release low levels of one or more therapeutic agents all the time. These cells would be preferentially placed in a containment vehicle, which would then be induced to release the therapeutic agent by an external stimulation device.

Delivery Devices

The drug-eluting cells can be carried by a variety of carriers for use in the delivery devices of the present invention. For example, intravascular stents and vascular grafts have been seeded with endothelial cells expressing recombinant t-PA, as disclosed in Dichek et al., *Circulation*, 8, 1347–1353 (1989) and Dichek et al., *Circulation*, 93, 301–309 (1996). In addition to stents and vascular grafts or stent grafts, suitable carriers for use in delivery devices of the present invention include, but are not limited to, synthetic patches, infusion sleeves, medical electrical leads and electrodes, and indwelling catheters.

Although any of these devices can be used as carriers for the drug-eluting cells, the following description focuses on stents. Whether the carrier is a stent or other medical device, the drug-eluting cells can be directly coated onto the carrier, incorporated into or onto a polymeric coating or film on the carrier, incorporated into microscopic containment vehicles and coated directly on the carrier or incorporated into or onto a polymeric coating or film on the carrier. As used herein, a "delivery device" includes the carrier (e.g., stent), cells that produce one or more therapeutic agents, and optional containment vehicles, as well as other optional therapeutic materials.

The term "stent" refers to any device capable of being placed into contact with a portion of a wall of a lumen. It includes classical stents used in intravascular applications, as well as any prosthesis that may be inserted and held where desired in a lumen. Such prostheses include single- or multi-filar braided mesh designs, metallic malleable designs, and others, as disclosed, for example, in International Patent Application No. WO 91/12779 (Medtronic, Inc.).

Typically, the stent has a lumen wall-contacting surface and a lumen-exposed surface. Where the stent is shaped generally as a tube-like structure, including a discontinuous tube or a ring-like structure, the lumen-wall contacting surface is the outside surface of the tube and the lumen-exposed surface is the inner surface of the tube. The stent can include polymeric elements, metallic elements, filametary elements, or combinations thereof. It can be coated with fibronectin or other extracellular matrix for adhering the cells to the stent. Preferably, the stent includes a fibrin or collagen coating or film or other natural or synthetic polymeric coating or film for holding the cells in place.

Figure 3:
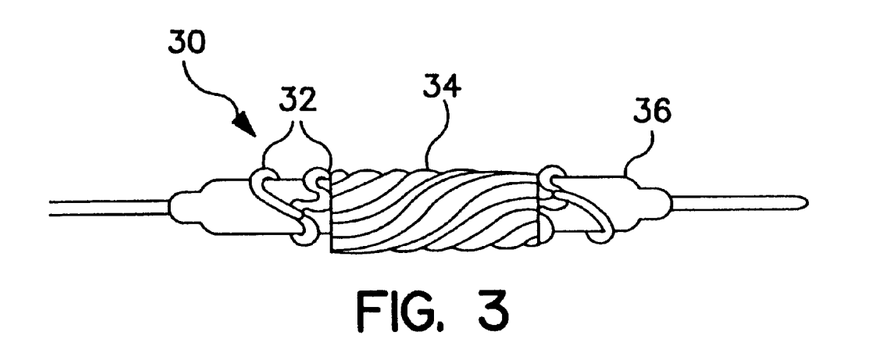
FIG. 3 is an elevational view of a preferred balloon catheter with stent including fibrin and drug-eluting cells according to the present invention.

A deformable metal wire stent useful as a stent framework to support the cells of this invention is disclosed in U.S. Pat. No. 4,886,062 (Wiktor). Other metallic stents useful in this invention include those of U.S. Pat. Nos. 4,733,655 (Palmaz) and 4,800,882 (Gianturco). FIG. 3 provides an elevational view of a preferred stent 30 of this invention. In one preferred embodiment, the stent comprises a stent framework 32 with a polymer film 34 (preferably, a fibrin film) extending circumferentially around at least a portion of the lumen-wall contacting surface of the stent and/or the lumen-exposed surface of the stent and preferably extending over substantially all of the lumen-wall contacting and lumen-exposed surfaces. A balloon 36 is positioned in FIG. 3 adjacent the lumen-exposed surface of the stent to facilitate delivery of the stent. Polymeric stents can also be used in this invention, whether they be nonbioabsorbable or bioabsorbable in part, or total.

The drug-eluting cells can be coated directly on the stent or they can be incorporated into a polymer film (i.e., sheeting) or coating. The stents of this invention preferably include a first polymer composition comprising fibrin or other polymer to provide containment for the drug-eluting cells. The first polymer composition of this invention can be prepared from a homopolymer, a copolymer (i.e., a polymer of two or more different monomers), or a composition (e.g., a blend) comprising fibrin with one or more polymers or copolymers, for example. The composition preferably forms a viscoelastic, tear-resistant, biocompatible polymer. The term "viscoelastic" refers to the prescribed "memory" characteristics of a molecule that allow the molecule to respond to stress as if the molecule was a combination of elastic solids and viscous fluids. The term "tear resistent" indicates that when the polymer is exposed to expansion stress, the material does not substantially tear. Tearing refers to the propagation of a nick or cut in the material while under stress. When the stent of this invention is expanded on a balloon, the polymer is able to expand to accommodate the balloon expansion. The term "biocompatible" is used herein to refer to a material that does not have toxic or injurious effects on biological systems.

Preferably, the first polymer composition minimizes or does not exacerbate irritation to the lumen wall when the stent is in position. The first polymer composition is preferably nonthrombogenic when applied alone or alternatively when used with anti-thrombogenic agents such as heparin, and the like, or with anti-inflammatory agents such as cyclosporins, and the like. The first polymer composition is also preferably a biostable or a bioabsorbable polymer depending on the desired rate of release or the desired degree of polymer stability.

The stents of this invention can be coated with fibrin, for example, by application of a fibrinogen solution and a solution of a fibrinogen-coagulating protein or by attachment of a fibrin preform or sleeve such as an encircling film of fibrin, including the film provided in U.S. Pat. No. 4,548,736 (Muller). As described in U.S. Pat. Nos. 4,548,736 (Muller) and 5,510,077 (Dinh et al.), fibrin is clotted by contacting fibrinogen with a fibrinogen-coagulating protein such as thrombin. The fibrinogen is preferably used in solution with a concentration of about 10 to about 50 mg/ml with a pH of about 5.89 to about 9.0 and with an ionic strength of about 0.05 to about 0.45. The fibrinogen solution typically contains proteins and enzymes such as albumin, fibronectin, Factor XIII, plasminogen, antiplasmin, and Antithrombin III. The thrombin solution added to make the fibrin is typically at a concentration of up to about 120 NIH units/ml with a preferred concentration of calcium ions between about 0.02 M and 0.2 M. Also preferably, the fibrinogen and thrombin used to make fibrin in the present invention are from the same animal or human species as that in which the stent of the present invention will be implanted to avoid cross-species immune reactions. The resulting fibrin can also be subjected to heat treatment at about 150° C., for about 2 hours to reduce or eliminate antigenicity.

The fibrin, or other polymer, can be in the form of a film produced by casting the combined fibrinogen and thrombin in a film and removing moisture from the film osmotically through a moisture permeable membrane. Alternatively, a substrate can be contacted with a fibrinogen solution and with a thrombin solution resulting in a fibrin film formed by polymerization of fibrinogen on the surface of the device. Multiple layers of fibrin applied by this method can provide a fibrin film in a variety of thicknesses. In another method, the fibrin can be first clotted and then ground into a powder that is mixed with water and stamped into a desired shape in a heated mold. These methods can be used with fibrin monomers or with combinations of monomers to form the first polymer composition of this invention. Those skilled in the art will recognize that the methods for forming the first polymer composition can be modified to include other polymers, as contemplated in this invention, without undue experimentation.

The first polymer compositions of this invention can include one or more other synthetic or natural polymers. Suitable polymers include those that are compatible with the cells and therapeutic agents. These include, but are not limited to, fibrins, collagens, alginates, polylactic acids, polyglycolic acids, celluloses, hyaluronic acids, polyurethanes, silicones, polycarbonates, mixtures or copolymers thereof, and a wide variety of other polymers typically disclosed as being useful in implantable medical devices. An example of a copolymer with improved structural strength and improved biological performance is a fibrin and polyurethane copolymer, as disclosed in U.S. Pat. No. 5,510,077 (Dinh et al.), or a fibrin alginate copolymer. Because fibrin is more readily degraded in the body than polyurethane, polyurethane can be used to regulate degradation of the fibrin covering the stent and to slow release of the cellular products from the stent.

Heparin, or other anticoagulants, such as polyethylene oxide, hirudin, and tissue plasminogen activator, can be incorporated into the stent prior to implantation in an amount effective to prevent or limit thrombosis. A heparin immersion procedure can be used to incorporate the heparin. A heparin solution can alternatively be added at the time that cells are loaded onto the stent. Heparin can also be incorporated into the polymer matrix before it has completely polymerized. For example, powdered heparin can be dusted onto the stent during the polymerization process and additional thrombin and fibrinogen can then be applied as a coating over the heparin.

The shape of the polymer film or coating can be modified based on the methods used to cover the stent. It can be spray coated onto the stent or a film can be molded over the stent framework. The first polymer composition of this invention can cover both the lumen wall contacting surface and the lumen-exposed surface of the stent.

Alternatively, a porous polymeric sheet material can be used into which fibrin is incorporated. The sheet could be prepared from polyurethane, for example, by dissolving a polyether urethane in an organic solvent such as 1-methyl-2-pyrrolidone; mixing into the resulting polyurethane solution a crystalline particulate material like salt or sugar that is not soluble in the solvent; casting the solution with particulate material into a thin film; and then applying a second solvent, such as water, to dissolve and remove the particulate material, thereby leaving a porous sheet. The porous sheet could then be placed into a fibrinogen solution in order to fill the pores with fibrinogen followed by application of a solution of thrombin and fibrinogen to the surface of the sheet to establish a fibrin matrix that occupies both the surface of the sheet and the pores of the sheet. Preferably, a vacuum would be pulled on the sheet to insure that the fibrinogen applied to the sheet is received into the pores.

The stent framework can also be positioned within a mold and the compounds forming the first polymer composition incorporated into the mold. The first polymer composition forming a sheet or sleeve can be prepared in an extended shape and then compressed or dehydrated into a final shape to fit over the stent. In this way, when the stent is expanded in place to fit the walls of a lumen, the first polymer composition can be readily expanded without tearing or introducing irregularities into the sleeve and/or the coating.

Figure 4:
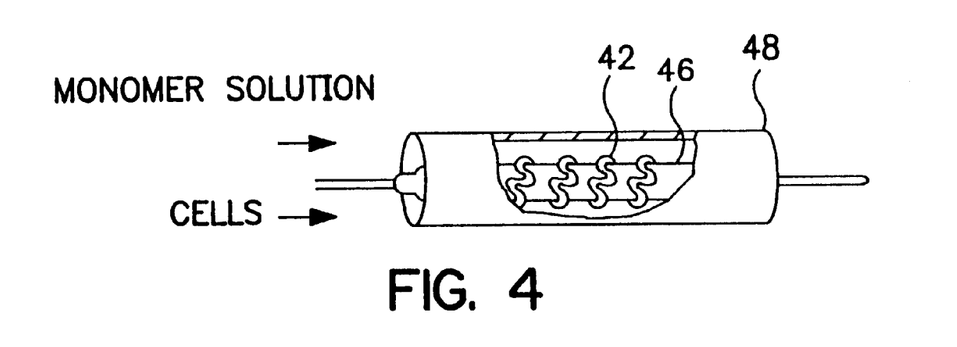
FIG. 4 illustrates a method of loading a stent with drug-eluting cells.

The stent can be loaded with drug-eluting cells by mixing the monomer solution of the first polymer composition with cells or by directly applying the cells to the polymerized composition. In a first embodiment, the stent is loaded with cells at the time of formation of the first polymer composition. FIG. 4 provides an example where a stent is formed over a balloon and introduced into a mold cavity to receive a solution sufficient to form the first polymer composition and including cells to be incorporated into the first polymer coating. In FIG. 4, the stent framework 42 is positioned over the balloon 46 and introduced into is a mold 48. A monomer solution capable of forming a first polymer composition is introduced into the mold along with the drug-eluting cells. Once the polymer is formed over the stent framework 42, the stent is released from the mold. The drug-eluting cells can also be included in a monomer solution as a spray or liquid coating to be applied to the stent framework.

Alternatively, the drug-eluting cells can be added to the polymer coated stent either at the time of stent manufacture or by the physician, prior to stent implantation. Where the first polymer composition is capable of dehydration and rehydration, the fibrin coated stent can be supplied in a sterile, dehydrated form and cells can be loaded onto the stent by rehydration of the first polymer composition positioned on the stent framework by immersing, wicking, or spraying a liquid suspension (such as a balanced salt solution, including HBSS or a tissue culture media, and the like) containing the cells onto the stent prior to stent implantation. The liquid used to deliver cells to the first polymer coating should support the stability of the cells and should include pH buffered solutions, stabilizers such as albumin, glycerol, or the like, in a form that is biocompatible and preferably nonimmunogenic.

In one embodiment, a dehydrated first polymer covered stent can be rehydrated in a solution of calcium chloride and sodium alginate containing the drug-eluting cells. The solution can be sprayed onto the stent, for example. A layer of calcium alginate then precipitates onto the surface of the stent with the cells. Alternatively, a dehydrated first polymer covered stent can be rehydrated in a solution of sodium alginate containing the drug-eluting cells, and then a layer of calcium alginate is sprayed or otherwise coated over the first polymer covering and cells. Where the cells are incorporated into a polymer solution for spray application or air pump applications, the polymer should be of sufficiently low viscosity to facilitate the application of the solution to the stent.

In another embodiment of the stents of this invention, a second polymer composition can be added over the first polymer composition following, or at the time of, cell loading. Preferably, the second polymer composition is biodegradable and the second polymer composition coats at least a portion of the first polymer composition and cells. For example, after the cells are loaded onto a stent having a first polymer composition coated thereon, the stent can be sprayed with or immersed in a solution to form a coating of a biodegradable polymer such as polylactic acid or methylcellulose, with or without heparin, or another coagulation inhibitory or anti-inflammatory compound. Advantageously, the second covering of polymer provides even greater sustained release capabilities and prevents loss of cells from the coated or covered stent during transit through the body to the target site on the body lumen. Suitable polymers for use in the second polymer composition include, but are not limited to, those listed above for the first polymer composition, and combinations thereof, and a wide variety of others typically disclosed as being useful in implantable medical devices.

One or more surfaces of the stent can be coated with one or more additional coatings of a polymer that is the same or different from the second polymer composition. Additional polymer coatings on the lumen-exposed surface are used to prevent release of the cells from the lumen-exposed surface of the stent when the stent is positioned in the body. This embodiment is particularly useful where the stent is used in the blood vasculature and in particular where the stent is used in the coronary artery.

The drug-eluting cells can also be included within a microscopic containment vehicle that can be stimulated to release the cells and/or their cellular products. This microscopic containment vehicle can be coated onto the delivery device directly or into or onto a polymer coating or film. The drug-eluting cells are enclosed within such a vehicle. Upon stimulation of the containment vehicle, the cells and/or cellular products (e.g., therapeutic agents) are released from the containment vehicle. Such containment vehicles are particularly desirable for cells that continuously produce and release the therapeutic agent. Thus, instead of stimulating the cells themselves, the containment vehicle is stimulated to release the cells and/or therapeutic agents. Stimulation of the containment vehicles can be accomplished using a variety of techniques.

Examples of microscopic containment vehicles include, but are not limited to, those described in International Patent Application Nos. WO 96/28841 (Ohman) and WO 96/34417 (Smela et al.), and in Smela et al., Science, 268, 1735–1738 (1995), which disclose micromachined structures and microactuators. In one example, such micromachined structures include conducting bilayers made of a layer of polymer and a layer of gold that are used as hinges to connect rigid plates to each other and to a silicon substrate. The bending of the hinges is electrically controlled and reversible, allowing precise three-dimensional positioning of the plates. The use of differential adhesion allows the structures to be released from the silicon substrate. Thus, complex shapes can be formed, such as cubes, of micrometer size that could be used to contain drug-eluting cells and their cellular products in association with a delivery device such as a stent, until they are needed for therapeutic or preventative treatment.

Microscopic containment vehicles can also include micropumps, reservoirs, with piezoelectric valves. The body of the pump and reservoir can be made of a polymeric material while the valves contain a piezoelectric material, which allows opening and closing of the valves and pumping movement by electrical stimulation. The reservoirs contain the drug-eluting cells and their cellular products. Upon stimulation of the piezoelectric material, the valve is opened to release the cells and/or cellular products. Implantable piezoelectric pumps are known (see, for example, U.S. Pat. No. 4,944,659 (Labbe et al.)) and can be modified by one of skill in the art to form containment vehicles for the present invention.

The stents of this invention can be provided in a sterile, dehydrated form, in a hydrated form with cells (shipped frozen or on ice) or as a first polymer covered stent supplied with the necessary materials to facilitate cells loading and further coating or covering of the stent as needed. Therefore, this invention also relates to a kit comprising a stent with a first polymer composition comprising fibrin, buffers suitable for rehydrating the stent and loading the cells and a container to facilitate sterile loading of the stent. Optionally, the kit can include further coatings or coverings to be applied over the first polymer composition. In a preferred embodiment, the kit includes: a stent comprising a lumen-wall contacting surface, a lumen-exposed surface, and a first polymer composition comprising fibrin covering at least a portion of the stent; a cell-loading composition to be applied to the stent; and a container to house the stent and the composition during application of the cell-loading composition.

Stimulating and Sensing Elements

Systems of the present invention include a second implantable device (i.e., a stimulation device) that includes a stimulating element, such as an implantable pulse generator (IPG) similar in many respects to pacemakers and defibrillators known in the art, for example, which is preferably in contact with a sensing element. This device monitors the patient to detect when a stimulus needs to be sent to the cells to trigger release of one or more therapeutic agents. This monitoring can be in the form of an electrocardiogram (ECG), for example, to detect an ST segment elevation or a reduction of blood flow in the coronary sinus. Once the onset of ischemia is detected, the stimulating element will trigger the release of cellular products. For example, when a blood clot is formed that reduces blood flow, an abnormal ECG is produced, which causes an IPG, for example, to trigger a stent to stimulate endothelial cells to release t-PA, which travels to the blood clot and dissolves it, thereby preventing myocardial infarction.

Cellular products can be released upon the action of a stimulus directly on the cells, particularly the cellular membrane, or on the microscopic containment vehicle in which the cells are optionally located. The cellular products, particularly the therapeutic agents, are then distributed to the desired site through a washing action of the delivery device with body fluids. Following stimulation of the cells or containment vehicle, cellular products can also be released by erosion or bioabsorption of the coated surfaces of the stent, for example, by dissolution of fibrin or hydrolysis resulting in crosslink cleavage and concomitant release of the physically entrapped cells.

The stimulation device can provide electrical stimulation, mechanical stimulation, acoustic stimulation, thermal stimulation, chemical stimulation, or combinations thereof, to the eukaryotic cells and/or the containment vehicles, for example. One of skill in the art will recognize that a variety of means of stimulation can be used to electrically, mechanically, acoustically, and/or chemically stimulate the cells and/or the containment vehicles. The following are presented as examples only and do not limit the specific mechanisms or devices by which the stimulation can occur.

Typically, electrical stimulation causes ions to flow through cells making their membranes permeable. If sufficient stimulation is applied, then large pores are created on the cellular membrane, which are sufficient for the cellular product to pass through. Electrical stimulation can occur as described herein with reference to FIG. 2.

Mechanical stimulation can be applied by twisting the cellular membranes of the cells, for example. This causes a shear force on the cells and elongates them. Surface area is not changed but the enclosed volume is decreased so the intracellular pressure increases, causing the contents of the cells to leak out. Alternatively, mechanical stimulation can be accomplished through the use of a piezoelectric material (e.g., a piezoelectric crystal) on the surface of the carrier of the delivery device. When an electrical pulse is applied to the crystal, it changes size (e.g., longer or shorter), which can stretch or compress the carrier, and hence cause pressure on the cells. Acoustic stimulation is similar to mechanical stimulation, but the pressure is applied repetitively by sound waves.

Thermal stimulation involves applying heat to the cells, which can cause them to release their cellular products. This can be accomplished by the use of resistive elements inside the carrier of the delivery device. When electrical current is applied, the resistive element applies heat to the cells.

Chemical stimulation involves releasing a compound (e.g., a ligand) into the blood stream that acts via a lock and key mechanism to interact with the cells. For example, a ligand can be released from the stimulation device and when it reaches the cells in the delivery device, it can attach to an appropriate receptor on the cells and trigger events leading to the release of the therapeutic agent.

Although current implantable pulse generators (IPGs) are designed to stimulate cardiac muscle tissue, they may be modified readily by one of skill in the art to stimulate drug-eluting cells in accordance with the teachings of the present invention. It will be appreciated that the stimulation device according to the present invention can include a wide variety of microprocessor-based implantable stimulators similar to those used in pacemakers, as disclosed in U.S. Pat. Nos. 5,158,078 (Bennett et al.), 5,312,453 (Shelton et al.), and 5,144,949 (Olson), and pacemaker/cardioverter/defibrillators (PCDs), as disclosed in U.S. Pat. Nos. 5,545,186 (Olson et al.), 5,354,316 (Keimel), 5,314,430 (Bardy), 5,131,388 (Pless), and 4,821,723 (Baker et al.).

Alternatively, the stimulation device can include stimulating elements similar to those used in implantable nerve or muscle stimulators, such as those disclosed in U.S. Pat. Nos. 5,199,428 (Obel et al.), 5,207,218 (Carpentier et al.), and 5,330,507 (Schwartz).

In general, the implantable stimulation device 22 shown in FIG. 2 includes a hermetically sealed enclosure that may include various elements, such as an electrochemical cell (e.g., a lithium battery) for providing electrical current to circuitry, circuitry that controls device operations, a telemetry transceiver antenna, and a circuit that receives downlinked telemetry commands from and transmits stored data in a telemetry uplink to an external programmer, in addition to other elements.

Figure 5:
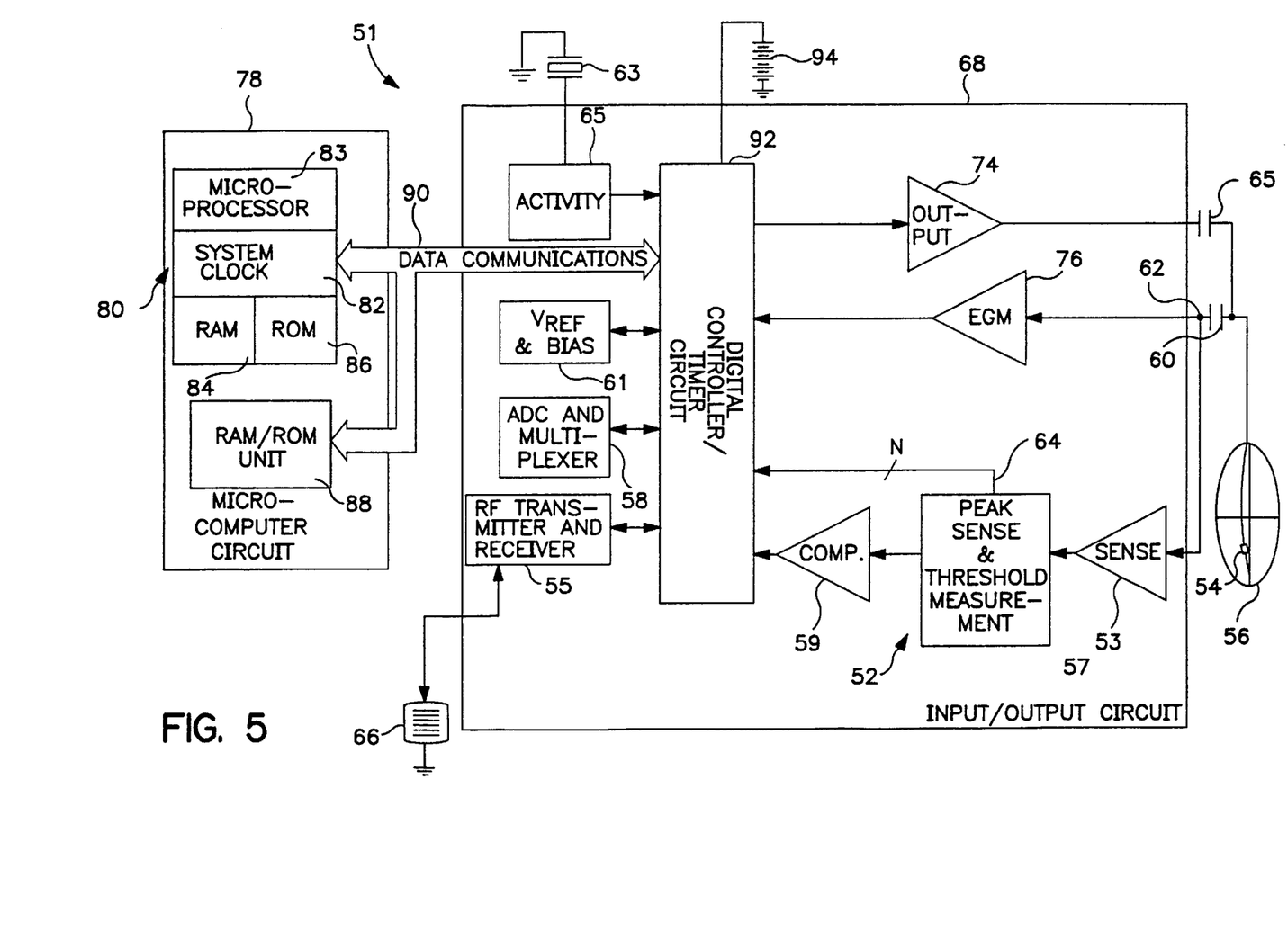
FIG. 5 shows a circuit for an implantable medical device according to the present invention.

FIG. 5 is a block diagram illustrating various components of an implantable stimulation device 22 which is programmable by means of an external programming unit (not shown). One such programmer easily adaptable for the purposes of the present invention is the commercially available Medtronic Model 9790 programmer. The programmer is a microprocessor device which provides a series of encoded signals to stimulation device 22 by means of a programming head which transmits radio frequency encoded signals according to a telemetry system, such as that described in U.S. Pat. No. 5,312,453 (Wyborny et al.), for example.

Stimulation device 22, illustratively shown in FIG. 5 as an exemplary embodiment, is electrically coupled to lead or antenna 24. Lead 24 may be used for stimulating only, or it may be used for both stimulating and sensing. Lead 24 is coupled to a node 62 in the circuitry of stimulation device 22 through input capacitor 60. Input/output circuit 68 also contains circuits for interfacing with stimulation device 22, antenna 66, and circuit 74 for application of stimulating signals to lead 24 under control of software-implemented algorithms in microcomputer unit 78.

Microcomputer unit 78 comprises on-board circuit 80 which includes system clock 82, microprocessor 83, and on-board RAM 84 and ROM 86. In this illustrative embodiment, off-board circuit 88 comprises a RAM/ROM unit. On-board circuit 80 and off-board circuit 88 are each coupled by a data communication bus 90 to digital controller/timer circuit 92. The electrical components shown in FIG. 5 are powered by an appropriate implantable battery power source 94 in accordance with common practice in the art. For purposes of clarity, the coupling of battery power to the various components of stimulating element 22 is not shown in the figures.

Antenna 66 is connected to input/output circuit 68 to permit uplink/downlink telemetry through RF transmitter and receiver unit 55. Unit 55 may correspond to the telemetry and program logic disclosed in U.S. Pat. No. 4,556,063 (Thompson et al.), or to that disclosed in the above-referenced Wyborny et al. patent. Voltage reference ($V_{REF}$) and bias circuit 61 generates a stable voltage reference and bias current for the analog circuits of input/output circuit 68. Analog-to-digital converter (ADC) and multiplexer unit 58 digitizes analog signals and voltages to provide "real-time" telemetry signals and battery end-of-life (EOL) replacement functions.

Sense amplifier 53 amplifies sensed signals and provides an amplified signal to peak sense and threshold measurement circuitry 57. Circuitry 57, in turn, provides an indication of peak sensed voltages and measured sense amplifier threshold voltages on path 64 to digital controller/timer circuit 92. An amplified sense amplifier signal is then provided to comparator/threshold detector 59. Sense amplifier 53 may correspond in some respects to that disclosed in U.S. Pat. No. 4,379,459 (Stein).

Circuit 92 is further preferably coupled to electrogram (EGM) amplifier 76 for receiving amplified and processed signals sensed by an electrode disposed on lead 24. The electrogram signal provided by EGM amplifier 76 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063. Note that lead or antenna 24 may be located in positions other than inside the heart.

Output pulse generator 74 provides stimuli to lead 24 through coupling capacitor 65 in response to a stimulating trigger signal provided by digital controller/timer circuit 92. Output amplifier 74, for example, may correspond generally to the output amplifier disclosed in U.S. Pat. No. 4,476,868 (Thompson).

It is to be understood that FIG. 5 is an illustration of an exemplary type of stimulation device which may find application in the present invention, or which may be modified for use in the present invention by one of skill in the art, and is not intended to limit the scope of the present invention.

In addition to a stimulating element within stimulation device 22, systems of the present invention include a sensing element for monitoring at least one physiological property to detect a change in a physiological condition (typically, the onset of ischemia caused by a decrease in blood flow due to an occlusion resulting from the rupture of unstable plaque). For example, a pseudo-surface electrocardiogram (ECG) using a subcutaneous electrode array can be used to detect a reduction in blood flow, which is represented by an abnormal morphology (e.g., inverted shape) of a T wave (i.e., the portion of an ECG pattern due to ventricular repolarization or recovery). Such a pseudo-surface ECG is similar to a normal ECG modified for implantation. In this sensing element, for example, an implantable pulse generator having three electrodes, each only about one centimeter apart, could be implanted into the pectoralis muscle in the chest of a patient. An ECG pattern, similar to that of a normal ECG, would be monitored for an indication of an abnormal morphology of a T wave.

Sensing elements can include one or more individual sensors for monitoring one or more physiological properties. In addition to a pseudo-surface ECG, such sensors include, for example, blood gas (e.g., $CO_2$) sensors, pH sensors, blood flow sensors in the coronary sinus, and the like. Other mechanisms of detection that can be used in sensors include, for example, acoustic time of flight changes as a result of flow, acoustic doppler, which takes advantage of the doppler effect (received frequency is different that the transmitted one), thermal dilution (a clinical technique to measure blood flow and cardiac output), and venous pressure drop due to lack of driving pressure from the blocked artery. Examples of sensors or implantable monitoring devices that can be modified to be used in the stimulation devices of the present invention are disclosed, for example, in U.S. Pat. Nos. 5,409,009 (Olson), 5,702,427 (Ecker et al.), and 5,331,966 (Bennet et al.). Suitable sensors and sensing techniques are well known to one of skill in the art and can be readily adapted for use in the present invention.

Figure 2A:
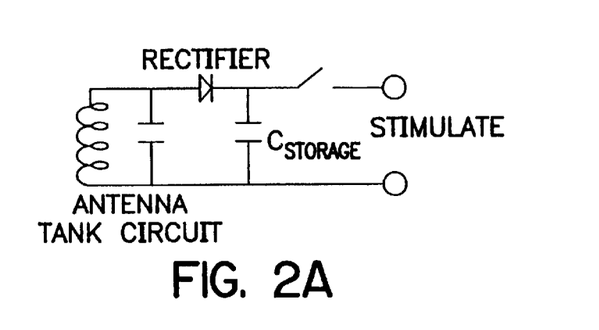
FIG. 2A is a diagramatic representation of a circuit in a coiled stent for electrically stimulating the cells in association with the stent.

For electrical stimulation, because the direct wiring from the stimulation device to the delivery device is not feasible, a telemetric communication system can be used. Such systems are known and can be modified to be used in the present invention. Examples of such systems are discussed above and described in U.S. Pat. No. 5,312,453 (Wyborny et al.), for example. Referring again to FIG. 2, the stimulation device 22 will produce a radio frequency (RF) signal 26 using lead 24 as a transmitting antenna, which is implanted into the right ventricle of a patient's heart. The lead 24 includes a coil, which transmits an H-field coupled pulse series (e.g., a 175 kilocycle, pulse position modulated, H-field signal) to the coil formed by stent 18, which is implanted into the left ventricle of a patient's heart. For a conversion of the magnetic field (H-field) into an electrical signal, the stent includes a metal coil with all but the ends coated with an insulating coating. A tuned LC filter integral with the stent 18 will receive some of this signal, rectify it, and when a sufficient charge is transferred from the stimulation device to the stent, energy will be used to electrically stimulate the engineered endothelial cells in the coronary artery to trigger the release of the therapeutic agent. Inset FIG. 2A is a representation of a circuit within the stent. This circuit includes an LC filter tuned to the specific frequency of the RF signal 26 for induction of electric current in the coiled stent 18 (or in a coil provided in the stent). A charge is stored in capacitor ($C_{storage}$) until a threshold voltage is reached, which activates a switch to close the circuit and cause current to flow through the cells associated with the stent. In such a system, the current density produced is preferably sufficient to stimulate the cells to release a therapeutic agent without significant damage to the cells or the therapeutic agents. Based on in vitro experiments, the current density for preferred embodiments is maintained below about 540 $\mu$-Amp/mm$^2$ and the current threshold below about 0.9 mA/mm$^2$ to avoid damage to the endothelial cells or the expressed product.

Thus, the delivery device that acts as a carrier for the drug-eluting cells can be powered with RF coupling. Alternatively, it can be self powered or battery powered.

EXAMPLES

The following examples are intended for illustration purposes only.

Electrical Stimulation Studies

Electrical and mechanical hardware were modified to enable the stimulation of endothelial cells cultured on inserts placed in tissue culture wells. The cells were stimulated with single pulses (1 millisecond long and delivered at a rate of 1 Hz) for 5 minutes a day, on 3 consecutive days. At the end of the 3 days, cells were removed from the culture wells, stained with crystal violet and photographed. Increases in the current density caused a decrease in the density of red stained endothelial cells. While a stimulation pattern that produced 540 $\mu$-Amp/mm$^2$ of current density appears to be detrimental to the endothelial cells, another pattern which produced 270 $\mu$-Amp/mm$^2$ of current density did not.

Studies continued to determine the stimulation parameters, and upper limits on the current density to prevent cell damage. By modifying the interface circuit between the stimulator and the tissue culture wells, the current densities in wells where endothelial cell cultures were grown were monitored. Below is a table summarizing the data.

| Well Number | Current Density Day 1 (mA/mm$^2$) | Current Density Day 2 (mA/mm$^2$) | Current Density Day 3 (mA/mm$^2$) | Observations |
|---|---|---|---|---|
| A1 | 2.10 | 1.99 | PULLED OUT | Zone of death on the near edge of the well closest to the outside electrode |
| A2 | 1.66 | 1.55 | PULLED OUT | Zone of death on the near edge of the well closest to the outside electrode |
| A3 | 1.77 | 1.66 | PULLED OUT | Zone of death on the near edge of the well closest to the outside electrode |
| A4 | 0.99 | 0.99 | PULLED OUT | Some floating cells, No significant cell death near outside electrode |
| A5 | 0.88 | 0.88 | PULLED OUT | Some floating cells, No significant cell death near outside electrode |
| A6 | 0.00 | 0.00 | PULLED OUT | Some floating cells, Cells appear to be healthy |
| B1 | 2.10 | 2.21 | 2.24 | Zone of death on the near edge of the well closest to the outside electrode |
| B2 | 1.35 | 1.33 | 1.55 | Zone of death on the near edge of the well closest to the outside electrode |
| B3 | 1.55 | 1.77 | 1.88 | Zone of death on the near edge of the well closest to the outside electrode |
| B4 | 0.84 | 0.88 | 1.11 | Starting to see cell death around the edge of the well closest to the outside electrode |
| B5 | 0.84 | 0.88 | 0.94 | Starting to see cell death around the edge of the well closest to the outside electrode |
| B6 | 0.00 | 0.00 | 0.00 | Some floating cells, Cells appear to be healthy |

By looking at the data shown above, 0.9–1.0 mA/mm$^2$ appears to be the current threshold for damaging the endothelial cells with in vitro electrical stimulation.

Cell Culture Studies

Example 1

Human coronary artery endothelial cells (Clonetics, San Diego, Calif.) were seeded in 24 well tissue culture plates at 1×10$^4$ cells/cm$^2$ (1.5 mL total volume) and grown in defined media as supplied by Clonetics. The cells were incubated at 37° C., 5% CO$_2$ for up to four days. The media was not changed on the cells during the course of the experiment. Supernatants from duplicate wells were withdrawn on days 2, 3, and 4 post-seeding. In addition, cells plus supernatants from a second set of samples were harvested from duplicate wells on days 2, 3, and 4 post-seeding. Samples were stored at –85° C. until assayed. The ELISA assay was performed on the test samples and on controls following the procedure outlined by the manufacturer (American Diagnostica, Inc.) The standard curve was generated using control plasma A, t-PA antigen control plasma set 2 (Product #275, American Diagnostica, Inc.). The test samples were assayed undiluted (20 $\mu$L assay volume). The results suggest that measurable t-PA was released from control endothelial cells, in the absence of stimulation. The levels of t-PA that were released were correlated to cell growth (more was measured after 4 days of culture than after 2 days).

Cell Culture Studies

Example 2

This experiment was performed similarly to the first experiment with the following changes. In the first part of the experiment, cells were seeded at three different densities ($1\times10^4$, $2\times10^4$, $4\times10^4$) in 0.5 mL total volume per well, and the cell supernatants were collected on day 2 and day 3 post seeding. In the second part of the experiment, cells were seeded at $2\times10^4$ cells/cm$^2$ and one group was stimulated once (on day 2 post seeding) and a second group was stimulated two times (once on day 2 and once on day 3 post seeding). The stimulation level was 55V (350–440 mA) for 5 minutes and supernatants were collected 15 minutes after stimulation. The following tables contain the data that was obtained from this experiment. The data confirms what was observed in the first experiment—that t-PA production/release is correlated with cell number and with cell growth. Although this data from the stimulated samples suggests that electrical stimulation at 55 volts for 5 minutes did not increase t-PA production/release as compared to the unstimulated control, it did not cause adverse effects on the released t-PA.

| Density | Day 2 | Day 3 | st dev | std |
|---|---|---|---|---|
| $1 \times 10^4$ | 15.153 | 23.208 | 0.088 | 1.73 |
| $2 \times 10^4$ | 33.164 | 41.219 | 5.9 | 1.566 |
| $4 \times 10^4$ | 44.773 | 54.926 | 3.309 | 1.755 |

| Condition | Day 1 | Day 2 | st dev | std |
|---|---|---|---|---|
| No Stim | 8.581 | 12.447 | 0.366 | 0.278 |
| 1x Stim | 8.08 | 10.86 | 0.54 | 0.176 |
| 2x Stim | | 11.264 | | 0.663 |

The complete disclosures of the patents, patent applications, and publications listed herein are incorporated by reference, as if each were individually incorporated by reference. The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An implantable system comprising:
    (a) a delivery device comprising:
        (i) an intraluminal stent comprising:
            (A) a lumen-wall contacting surface;
            (B) a lumen-exposed surface;
            (C) a first polymer composition covering at least a portion of the stent; and
        (ii) endothelial cells associated with the first polymer composition; wherein the endothelial cells produce at least one therapeutic agent;
    (b) an electrical stimulating element operatively coupled to the delivery device for stimulating the release of the therapeutic agent from the delivery device; and
    (c) a sensing element for monitoring at least one physiological property of a patient in which the system is implanted and communicating with the electrical stimulating element to stimulate the release of the therapeutic agent from the delivery device.

2. A method of local delivery of a therapeutic agent comprising:
    (a) providing an implantable system comprising:
        (i) a delivery device comprising:
            (A) an intraluminal stent comprising:
                (I) a lumen-wall contacting surface;
                (II) a lumen-exposed surface;
                (III) a first polymer composition covering at least a portion of the stent; and
            (B) endothelial cells associated with the first polymer composition;
            wherein the endothelial cells produce at least one therapeutic agent;
        (ii) an electrical stimulating element operatively coupled to the delivery device for electrically stimulating the release of the therapeutic agent from the delivery device; and
        (iii) a sensing element for monitoring at least one physiological property of a patient in which the system is implanted and communicating with the stimulating element to stimulate the release of the therapeutic agent from the delivery device; and
    (b) implanting the implantable system into the body of a patient; wherein the therapeutic agent is released from the delivery device when the sensing element detects a predetermined level of a physiological property and communicates with the electrical stimulating element to trigger the release of the therapeutic agent.

3. A method of making an implantable system for local delivery of a therapeutic agent, the method comprising:
    (a) providing a delivery device comprising a carrier and eukaryotic cells that produce at least one therapeutic agent;
    (b) providing a stimulating element operatively coupled to the delivery device for stimulating the release of the therapeutic agent from the delivery device;
    (c) providing a sensing element for monitoring at least one physiological property of a patient in which the system is implanted; and
    (d) connecting the stimulating element and sensing element such that they communicate with each other to stimulate the release of the therapeutic agent from the delivery device when implanted in the body of a patient and the sensing element detects a predetermined level of a physiological property.

4. The method of claim 3 wherein the step of providing a delivery device comprises:
    (a) providing a carrier;
    (b) isolating eukaryotic cells from a patient;
    (c) culturing the eukaryotic cells;
    (d) delivering nucleic acid of a desired therapeutic agent to the eukaryotic cells to form genetically engineered eukaryotic cells; and
    (e) contacting the carrier with the genetically engineered eukaryotic cells.

5. The method of claim 4 wherein the eukaryotic cells are endothelial cells.

6. The method of claim 5 wherein the nucleic acid encodes tissue plasminogen activator.

7. The method of claim 4 wherein the step of delivering nucleic acid comprises infecting the eukaryotic cells with a retrovirus comprising the nucleic acid to form genetically engineered eukaryotic cells.

8. The method of claim 4 wherein the nucleic acid is RNA or DNA.

9. The method of claim 4 wherein the carrier comprises a stent comprising a lumen-wall contacting surface, a lumen-exposed surface, and a first polymer composition comprising fibrin covering at least a portion of the lumen-exposed surface to form a polymer covered stent.

10. The method of claim 9 wherein the contacting step comprises dipping the polymer covered stent into a solution or gel comprising the genetically engineered eukaryotic cells.

11. The method of claim 9 wherein the contacting step comprises placing the first polymer composition and genetically engineered eukaryotic cells into a mold.

12. The method of claim 9 wherein the eukaryotic cells are contacted with the stent just prior to implantation.

* * * * *